United States Patent
Kelly et al.

[11] Patent Number: 6,157,851
[45] Date of Patent: *Dec. 5, 2000

[54] ELECTRODERMAL POSITIONING DEVICE AND PROCESS OF MAKING SAME

[75] Inventors: Robert J. Kelly, Camarillo, Calif.; William K. Wenger, Weehawken, N.J.

[73] Assignee: Unilead International, Inc., Orinda, Calif.

[*] Notice: This patent is subject to a terminal disclaimer.

[21] Appl. No.: 09/186,161

[22] Filed: Nov. 5, 1998

Related U.S. Application Data

[63] Continuation of application No. 08/783,904, Jan. 16, 1997, Pat. No. 5,865,741, which is a continuation-in-part of application No. 08/508,928, Jul. 28, 1995, abandoned.

[51] Int. Cl.[7] ................................................. A61B 5/0402
[52] U.S. Cl. .......................... 600/386; 600/391; 600/393
[58] Field of Search ................................... 600/372, 383, 600/386, 389, 390, 391, 392, 393

[56] References Cited

U.S. PATENT DOCUMENTS

| | | | |
|---|---|---|---|
| D. 313,652 | 1/1991 | Lavine | D24/17 |
| 3,910,260 | 10/1975 | Sarnoff et al. | 128/2.06 R |
| 4,102,331 | 7/1978 | Grayzel et al. | 128/2.1 E |
| 4,328,814 | 5/1982 | Arkans | 128/640 |
| 4,353,372 | 10/1982 | Ayer | 128/640 |
| 4,522,211 | 6/1985 | Bare | 128/640 |
| 4,583,549 | 4/1986 | Manoli | 128/640 |
| 4,608,987 | 9/1986 | Mills | 128/639 |
| 4,674,511 | 6/1987 | Cartmell | 128/640 |
| 4,763,660 | 8/1988 | Kroll et al. | 128/640 |
| 4,957,109 | 9/1990 | Groeger et al. | 128/640 |
| 5,042,481 | 8/1991 | Suzuki et al. | 128/639 |
| 5,058,589 | 10/1991 | Ding et al. | 128/640 |
| 5,184,620 | 2/1993 | Cudahy et al. | 128/639 |
| 5,191,886 | 3/1993 | Paeth et al. | 128/640 |
| 5,224,479 | 7/1993 | Sekine | 128/644 |
| 5,257,631 | 11/1993 | Wilk | 128/710 |
| 5,293,867 | 3/1994 | Oommen | 600/383 |
| 5,307,818 | 5/1994 | Segalowitz | 128/696 |
| 5,327,888 | 7/1994 | Imran | 128/640 |
| 5,341,806 | 8/1994 | Gadsby et al. | 128/640 |
| 5,370,116 | 12/1994 | Rollman et al. | 128/644 |
| 5,465,727 | 11/1995 | Reinhold, Jr. | 128/710 |
| 5,507,290 | 4/1996 | Kelly et al. | 128/640 |
| 5,518,007 | 5/1996 | Becker | 600/544 |
| 5,546,950 | 8/1996 | Shoeckert et al. | 128/696 |
| 5,678,545 | 10/1997 | Stratbucker | 128/640 |
| 5,865,741 | 2/1999 | Kelly et al. | 600/386 |

FOREIGN PATENT DOCUMENTS

| | | |
|---|---|---|
| 122258 | 6/1972 | Denmark . |
| 0275811 | 7/1988 | European Pat. Off. . |
| 2619300 | 2/1989 | France . |

*Primary Examiner*—Lee Cohen
*Attorney, Agent, or Firm*—Fitzpatrick, Cella, Harper & Scinto

[57] ABSTRACT

A template has a flexible sheet with a fixed dimensional array $V_1$–$V_6$ positioned in a specific size configuration appropriate for standard electrocardiographic recording. The distance between $V_1$ and $V_2$ is 2.00 inches±0.56 inches, and the distance between $V_2$ and $V_4$ is 3.5 inches±1.00 inch, with $V_3$ located substantially midway between $V_2$ and $V_4$, and $V_5$ is equidistant between $V_4$ and $V_6$.

48 Claims, 7 Drawing Sheets

ELECTRODERMAL POSITIONING DEVICE AND PROCESS OF MAKING SAME

RELATED U.S. APPLICATION

This application is a continuation of application Ser. No. 08/783,904, filed Jan. 16, 1997, now U.S. Pat. No. 5,865,741, issued Feb. 2, 1999, which is a continuation-in-part of application Ser. No. 08/508,928, filed Jul. 28, 1995, now abandoned.

BACKGROUND OF THE INVENTION

1. Field of the Invention

This invention relates to a disposable medical device for use when employing electrical signals to monitor or stimulate various parts of the body. More particularly, the present invention involves a template device for assistance in establishing electrical connection to a patient's skin. The template can be used in conjunction with a plurality of electrode connectors or electrodeless connectors and an electrocardiological measuring apparatus.

2. Description of the Prior Art

Prior art medical electrodes generally are combination structures including a metallic or otherwise conductive support member to which an electric wire from an assorted apparatus may be attached. Generally, electrocardiograms sometimes referred to as an EKG or ECG have ten cable leads which attach to various points on the upper and mid-torso of a patient to measure and analyze cardiac data.

Of primary concern when preparing for an electrocardiogram is accurate placement of the electrodes. The person responsible for attaching the electrodes and lead wires ("leads") of the EKG often has problems in attaching these multiple leads to the patient because the lead wires may tangle with one another or, in the case of suction-type electrodes, may become detached before or after they are all connected. Accurately placing and securing a large number of leads can be difficult and time consuming and requires the knowledge of a skilled technician or physician.

Periodic electrocardiograms can provide a cardiographic profile of a patient for early detection and diagnosis of cardiovascular diseases. For purposes of providing an accurate profile, it is important not only that the electrocardiogram be taken with sensors affixed accurately, but that the sensors are placed at the same location on the patient as for the previous electrocardiograms. The accuracy of the reproducible results is critical so that a series of electrocardiograms can be compared, between testing episodes, to provide a continuing profile of a patient for diagnosis and treatment of heart disease.

A full screen, ten electrode (twelve lead) electrocardiograph provides the most accurate picture for recognizing ischemic electrocardiographic changes. However, in urgent situations, including those electrocardiograms taken during an acute symptomatic episode of a cardiac patient, only two to four electrodes may be attached to the patient. Therefore, it would be advantageous and desirable to have a device which enables more leads to be accurately placed and quickly secured during an acute symptomatic episode.

On the other hand it may be necessary to quickly remove certain or all of the chest leads of the EKG when a patient is experiencing another heart attack in order to administer CPR, to massage the heart, administer drugs or apply electrical defibrillation paddles. Accordingly, valuable seconds are often lost in removing the chest leads of the EKG device in order to administer aid to the patient.

U.S. Pat. No. 4,328,814 to Arkans teaches a plurality of electrodes arranged in a strip. Each electrode has a conductive lead which runs to a single junction connector having one cable leading to the EKG device. This device is designed for an adult patient so that patients having larger or smaller torsos will have difficulty in using the device because the electrodes cannot be easily adjusted to accommodate a smaller or larger torso.

U.S. Pat. No. 4,353,372 to Ager discloses a plurality of electrodes which plug into a junction box connected to an EKG machine. Each of the electrodes includes wires molded into a central cable system which joins the junction box. This device does not include means for quickly attaching or removing the electrodes. For example, in an emergency situation if the electrodes must be removed quickly, the junction box must be disconnected first and then each of the electrodes must be detached. Although each electrode has a wire lead from the main molded cable, which may permit some adjustment in the placement of the electrodes on the upper portion of a human torso, the device is not entirely adequate for large adults or very small children because of the limited adjustment of each electrode.

U.S. Pat. No. 4,608,987 to Mills relate to a vest-like garment having a plurality of apertures adapted for receiving associated electrodes. However, the vest is not tailored for a specific patient and proper fit is provided by adjustable straps which may be secured by VELCRO material. Therefore, there is no assurance that the electrodes are placed at the same anatomical location upon reuse with the same patient.

U.S. Pat. No. 3,910,260 describes telephonic units for transmitting EKG signals to ECG receiving equipment which could be at a hospital or a physician's office. The transmission may take place in emergency vehicles where prior medical history may not be readily available. In order to obtain meaningful and reliable data ECG signals are necessary for the care providers. None of the prior art devices have disclosed a low cost solution for obtaining repeatable placement of sensors for accurate and readable ECG signals in the field by unskilled individuals.

U.S. Pat. No. 4,583,549 to Manoli relates to an ECG electrode pad having a flexible non-conductive pad provided with a plurality of electrodes. In this patent, the electrodes are positioned at various anatomically defined positions on the chest wall. Although different size pads are contemplated, this patent lacks any teaching or suggestion of how the sizes are dimensioned, how they would be determined, or even how a patient would be fitted with the proper size.

Because of the inadequacies of prior art devices there is a need for a system which prevents EKG electrode leads from being entangled; provides quick removal of some of the electrodes while leaving the remaining electrodes in position when it is necessary to administer aid to a patient having a heart attack; provides accurate repeatable placement of electrodes at substantially the same anatomical location; accurately and repeatedly obtains signals from body electrodes by efficient and effective electrical transmission; may be attached by unskilled persons; and may be available in various sizes to accommodate to fit the patient.

SUMMARY OF THE INVENTION

The present invention, in one aspect involves a disposable non-conducting flexible sheet having a predetermined dimensional array. The flexible sheet serves as a template for aligning connectors, either of the electrode type or electrodeless type, on the chest of a patient for transmitting (receiving or sending) electrical impulses.

More particularly, this aspect of the invention relates to a disposable template comprising a flexible non-conductive sheet having a predetermined dimensional array $V_1$–$V_6$. The dimensional array is sized such that $V_1$ and $V_2$ are positioned approximately on either side of the sternum at the fourth intercostal space and array $V_3$ is positioned midway between $V_2$ and $V_4$. $V_5$ is equidistant between $V_4$ and $V_6$. The distance between $V_1$ and $V_2$ is about 2.00 inches±0.56 inches, i.e., $V_1$ is 1.00 inch±0.28 inches to the right and $V_2$ is 1.00 inch±0.28 inches to the left, measured equidistantly from the centerline of the sternum. The distance between $V_2$ and $V_4$ is about 3.5 inches±1.00 inch, and $V_3$ is located substantially midway between $V_2$ and $V_4$.

In another aspect of the invention, the flexible non-conductive sheet is provided in a plurality of sizes, with each size having arrays $V_1$, $V_2$, $V_3$ and $V_4$ at substantially the same locations and having arrays $V_5$ and $V_6$ at different locations depending on size. In this regard, the locations of $V_5$ and $V_6$ are based on a measured distance between a midclavicular line and a midaxillary line on the chest of the patient.

In yet another aspect of the present invention, the dimensional array on the flexible non-conductive sheet is provided with cutouts. The template is placed on the patient's chest and then conventional electrodes can be positioned in the cutouts.

In still another aspect of the present invention, the template can be provided with a plurality of conventional tab electrodes affixed on their top sides to the flexible sheet to be placed against the patient's chest. The electrodes are positioned at the predetermined dimensional array. Small cutouts, or openings, in the template expose the electrode tabs for attaching lead wire clips.

In yet another aspect of the invention, top sides of individual electrodes are lightly affixed to the flexible sheet of material, also at the a predetermined dimensional array. The sheet is placed on the patient's chest and then peeled away, leaving the electrodes properly located on the chest.

In still another aspect of invention, disclosed is a method of sizing a patient for fitting a template having a flexible sheet with a fixed dimensional array $V_1$–$V_6$ positioned in a specific size configuration appropriate for standard electrocardiographic recording, with the distance between $V_1$ and $V_2$ being 2.00 inches±0.56 inches, and the distance between $V_2$ and $V_4$ being 3.5 inches±1.00 inch, with $V_3$ located substantially midway between $V_2$ and $V_4$, and $V_5$ being equidistant between $V_4$ and $V_6$. The method comprises the steps of measuring the distance between the midclavicular line and a midaxillary line on the chest of the patient, and selecting a template size based on the measured distance.

These and other objects, aspects, features and advantages of the present invention will become apparent from the following detailed description of the preferred embodiments taken in conjunction with the accompanying drawings.

DESCRIPTION OF THE PREFERRED EMBODIMENTS

Figure 1:
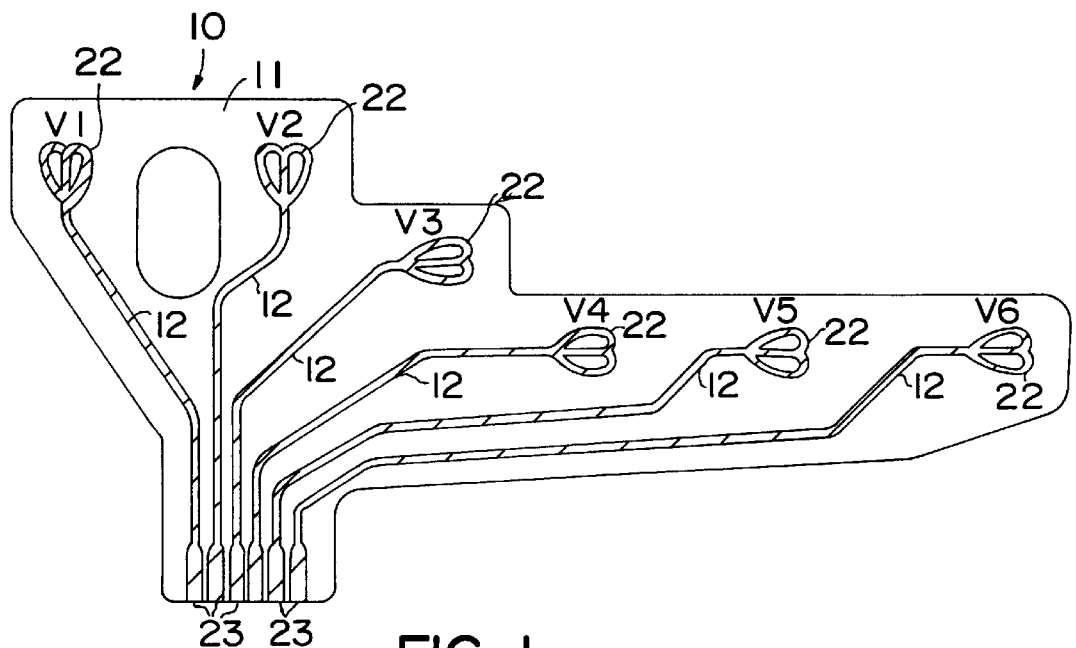
FIG. 1 shows a preferred template device of the present invention provided with end sensors for attachment to the torso of a patient.
Figure 5:
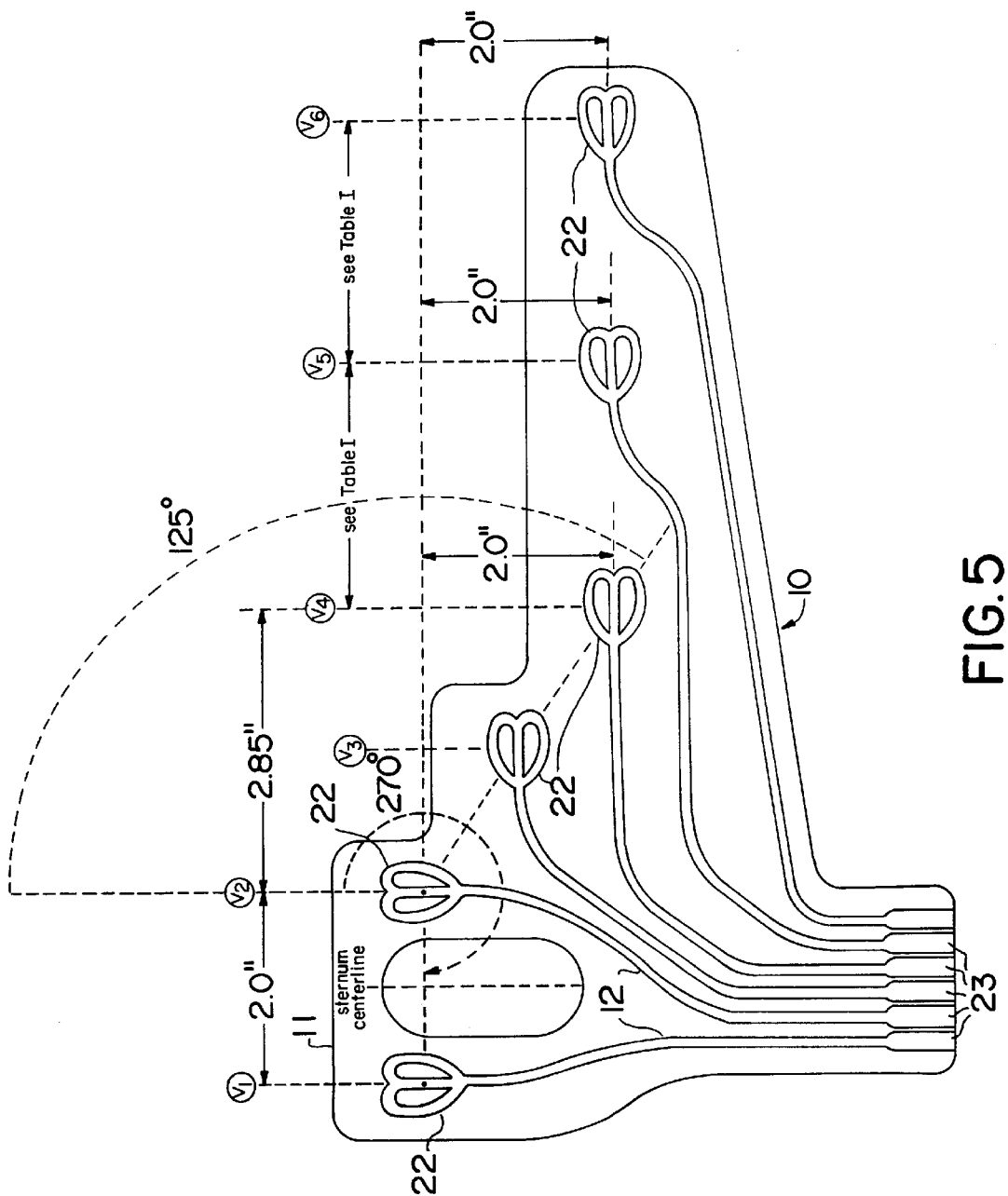
FIG. 5 illustrates the positioning of a dimensional array on the template device according to this invention.

Referring now to the drawings, FIGS. 1 and 5 illustrate a template 10 in accordance with a first embodiment of the invention. In this embodiment, an array of electrodeless receptors 22 are positioned at a predetermined dimensional array $V_1$–$V_6$ on the template.

FIG. 1 illustrates the template 10 of the present invention for placement on the chest of a patient. The template is formed of a flexible non-conducting sheet 11 which, in this non-limiting example, incorporates multiple conductor strips 12 for connection to a standard electrocardiographic receiving unit. The non-conducting sheet 11 includes conductor strips 12 which form end sensors or receptors 22 which are positioned on the sheet and spaced relative to each other, whereby the receptors 22 are positioned in a specific size configuration appropriate for electrocardial recordings. Each strip 12 includes a receptor 22 at a first end portion adapted for electrical connection with the skin for receiving and transmitting electrical impulses generated by the body. A second end of each strip 12 at the terminal connector end 23 engages a common electrical connection or cable junction (not shown) for connection with the electrocardiograph device (not shown).

When in use, an electrically conductive ink containing a biocompatible adhesive gel is applied to the body contacting side of sheet 11 at each receptor 22 of connector 12 for adhesion to the skin of the patient for providing electrical connection between each of the precordial ends and the terminal end 23 connected to the proper receiving devices (not shown).

The adhesive gel coated area of the connector device includes at least one release liner in releasable adhesive contact with the gel. Each of the conductor strips 12 are less than 10, and preferably less than 5, micrometers in thickness, whereby the flexibility of the connector and adhesion of the gel surface to the skin are substantially enhanced.

FIG. 1 shows the connector array ($V_1$, $V_2$, $V_3$, $V_4$, $V_5$, and $V_6$) on the flexible sheet 11 which is designed to adhere to a human torso so that the receptors 22 are located below the sternum, over the epigastric region of the abdomen and near the centerline of the torso. The flexible sheet 11 can be substantially transparent and includes an opening in the proximate center which is intended to span the upper portion of the sternum of the patient. The sheet may include indicia adjacent to or on each of the conductor strips to facilitate correct placement of the receptors on the precordial areas of the human torso.

Figure 2:
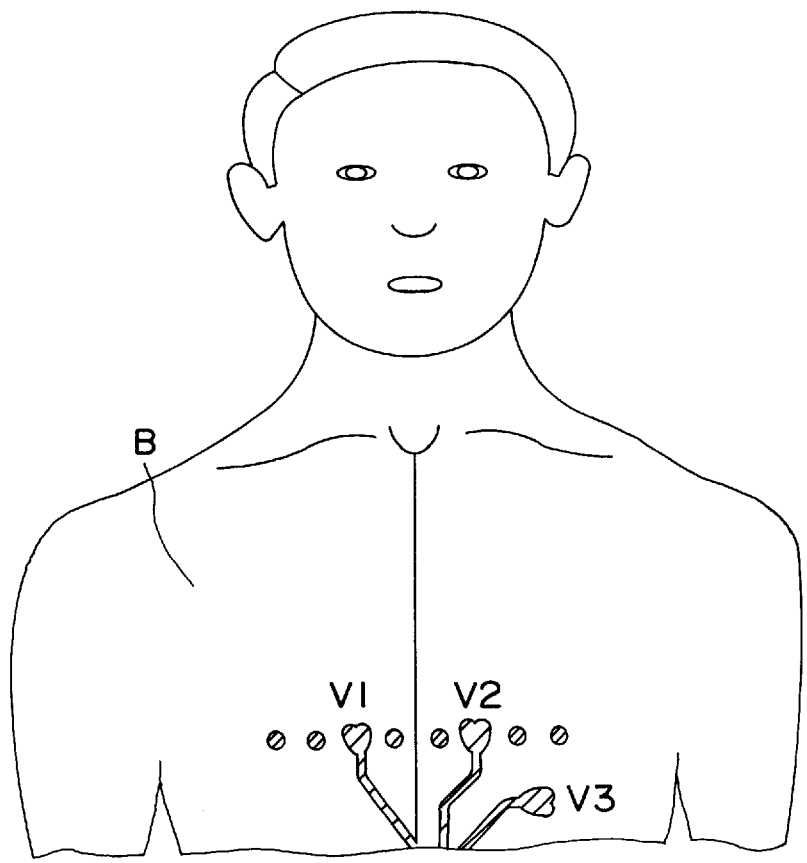
FIG. 2 shows a portion of the device illustrated in FIG. 1 as it is properly positioned on a patient.

FIG. 2 illustrates the position of the electro-dermal connector device 10 as it is properly positioned upon a patient. The connector device 10 is generally attached by adhering the precordial receptors. The receptors at $V_1$ and $V_2$ are attached approximately on opposite sides of the sternum at the fourth intercostal space. The receptors at $V_3$ and $V_4$ are attached over the ribs, with $V_3$ positioned approximately equidistant between $V_2$ and $V_4$. The receptors at $V_5$ and $V_6$ are placed at the side of the torso so that $V_5$ is substantially midway between $V_4$ and $V_6$. For small sizes the distance between $V_4$ and $V_6$ is on the average of 3.5 inches, for medium sizes 5.0 inches and for large sizes 7 inches. Of course, these measurements have a degree of tolerance, e.g., ±1.0 inch, to provide a range within which the connector device operates effectively. It should also be appreciated that distances between any of the receptors that fall outside the ranges disclosed herein are still considered to be within the scope of the invention as long as an effective, easy to use connector device is provided in consonance with the disclosed invention. The contour of the template 10 is configured to conform substantially to the shape of a human trunk.

In cross section a preferred laminate of the invention comprises the following layers:

a) a flexible non-conductive film of polyethylene terphthalate;

b) catalyst layer in contact with silver ink;

c) a connector strip comprised of silver ink;

d) a dielectric layer in contact with silver ink;

e) a conductive hydrogel layer superimposed upon the silver ink layer; and f) a flexible release liner as the top layer superimposed upon the conductive hydrogel.

The flexible non-conductive web or sheet 11 may be formed from any non-conductive flexible natural or synthetic sheet material which is capable of accepting a print. Generally any cellulosic material, polyester, polyolefin, polyvinyl chloride, nylon or mixtures thereof would be suitable. Cotton, polypropylene, polyethylene can be used because of cost. However, polyester is most preferred. The polymer sheet material may be color coded for specific body areas or may contain an outline and/or color markings to simplify attaching or positioning of the electro-dermal connector device. As mentioned earlier the device of this invention is designed to include the use by an untrained or trained individual. This device allows an untrained person including the patients themselves to obtain highly reliable and repeatable ECG signals.

The receptors 22 can be produced from any electrically conductive material, e.g., metals, conductive polymers, graphite, carbon fibers and the like. Conductive materials such as gold, copper, silver, tin, aluminum, N-vinyl pyrrolidone and alloys or mixtures thereof may be used. The receptors can be made of metal foil or made from a conductive paste of a metal in particle form in a suitable binder which is printed or silk screened onto the flexible non-conductive sheet. The connective polymer may be heat pressed or otherwise conventionally adhered to the web or sheet.

Copper strips may be electrolessly deposited on the polymeric sheets in a range of thickness from about 0.25 to about 5 microns, more preferably from 0.25 to 1.5 microns and most preferably 0.4 microns in thickness.

If desired, the exposed conductive strips may be partially coated with a dielectric polymeric material so that only selective portions are exposed. Suitable dielectric coatings include polyesters, ethylene-vinyl acetate copolymers, polyvinyl chloride and its copolymers, terpolymers such as acrylonitrile-butadiene styrene (ABS resins) and inter alia.

Preferable to copper, however, a metallic ink may be used, such as a silver ink commercially available and marketed by Dupont Chemical Corp. of Wilmington, Del. under the tradename Composition 9793.

One conductive adhesive hydrogel used is manufactured by Polyflex Circuits. Other suitable conductive adhesives are sold commercially by Lec Tec Corporation of Eden Prairie, Minn. and by 3M Corporation of St. Paul, Minn. Although an adhesive hydrogel is preferred any commercial electro-dermal adhesive would be operable. Preferably the area size of the hydrogel is between about 3 and 9 square centimeters.

The flexible release liner may be made from a suitable dielectric film or coated paper which includes polyesters, olefinic polymers, polyvinyl chloride and its copolymers, acrylic rubbers, ABS resin and the like.

In this embodiment the template 10 comprises at least six gel contact areas and is adapted for use in electrocardiography.

In accordance with the present invention, the template 10 is available in various sizes. More specifically, by properly positioning the dimensional array $V_1$–$V_6$, a template having three sizes (small, medium and large) is sufficient to accommodate nearly any size adult person. In positioning the array, it has been found that the distance between connectors $V_1$ to $V_4$ is generally consistent for all three sizes. The dimensions between $V_1$, $V_2$, $V_3$ and $V_4$ have been developed to accommodate nearly all adults within tolerances acceptable for the resting ECG. It has also been found that body placement for connectors $V_5$ and $V_6$ vary depending on individual size. Although in this embodiment three sizes are disclosed, it will be appreciated that templates of different sizes are well within the scope of the invention.

Figure 4:
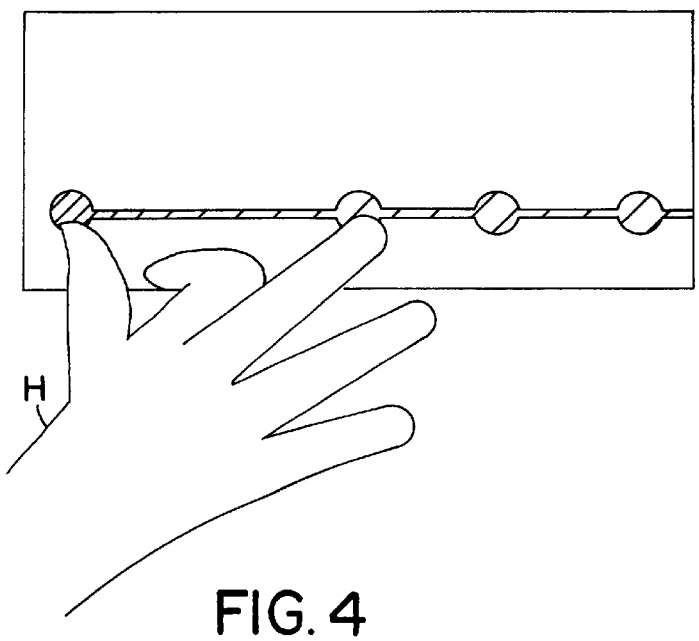
FIG. 4 shows another step in the method for determining the size of the device to be placed on a patient according to this invention.
Figure 3:
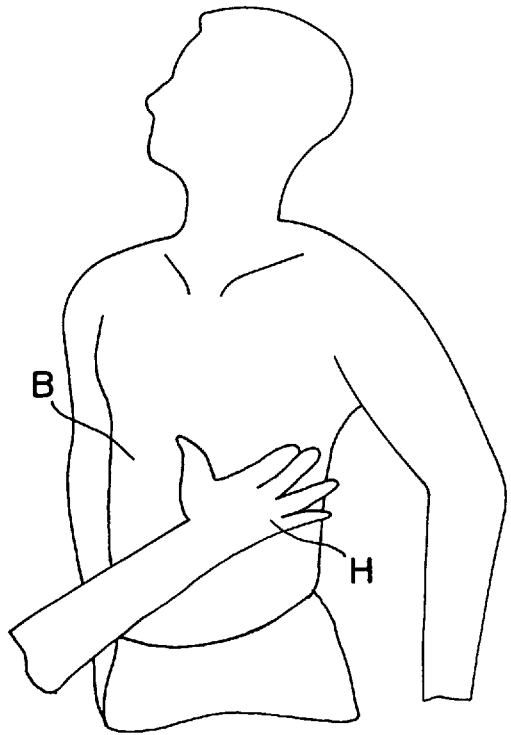
FIG. 3 illustrates the first step in the method for determining the size of the device to be used on a patient according to this invention.

FIG. 3 shows a method of determining the proper size. In this figure, the measurement M from the $V_4$ position to the $V_6$ position determines the size of the device. This measurement can be determined by having the technician measure, such as by using his/her thumb and the middle finger, the distance between the midclavicular line and midaxillary line on the chest of the patient. This distance is then matched to a scale provided as shown in FIG. 4. The table below corresponds to the illustrated scale.

TABLE I

| SIZE | $V_4$–$V_5$ | $V_5$–$V_6$ |
|---|---|---|
| Small | 1.75" | 1.75" |
| Medium | 2.50" | 2.50" |
| Large | 3.50" | 3.50" |

Generally, the size of the vest is determined by the distance between $V_4$ to $V_6$. That is, the distance between the midclavicular line and the midaxillary line on the patient. For a small or device the distance between $V_4$ and $V_6$ can range from about 2.5 to 4.5 inches, for the medium vest the distance can range from about 4.0 to 6.0 inches, and for the large device the distance can range from about 6.0 to 8.0 inches.

Figure 6:
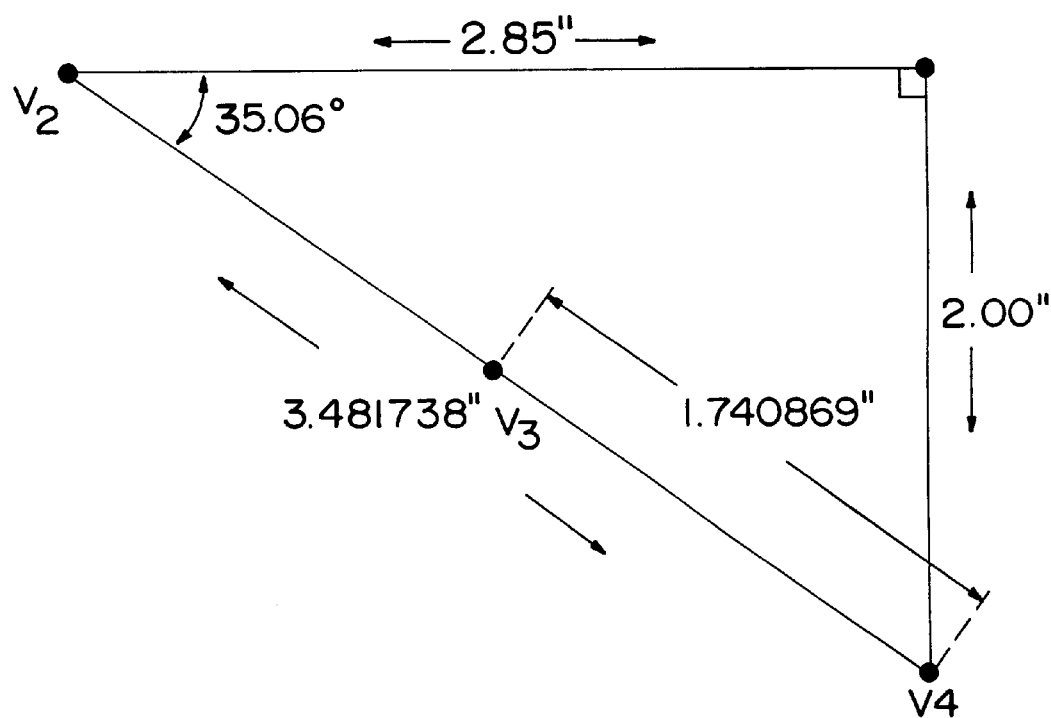
FIG. 6 shows preferred dimensions of receptors $V_2$, $V_3$ and $V_4$ in the dimensional array.

In all sizes of the device of the invention, $V_1$, $V_2$, $V_3$ and $V_4$ are generally positioned the same. With reference to FIG. 5, the center of $V_1$ is located on a point generally about 2.00 inches±0.56 inches from the center of $V_2$ approximately on the 270 (90) degree radial from the center of $V_2$ wherein the radial is measured with zero degrees from the top of $V_2$. The center of $V_4$ is located on a point generally 3.5 inches±1.00 inch from the center of $V_2$ approximately on the 125 (235) degree radial from the center of $V_2$. The center of $V_3$ is in line with $V_2$ and $V_4$ and is located on a point substantially between the center of $V_2$ and the center of $V_4$. FIG. 6 shows preferred dimensions for $V_2$, $V_3$ and $V_4$.

Figure 7A:
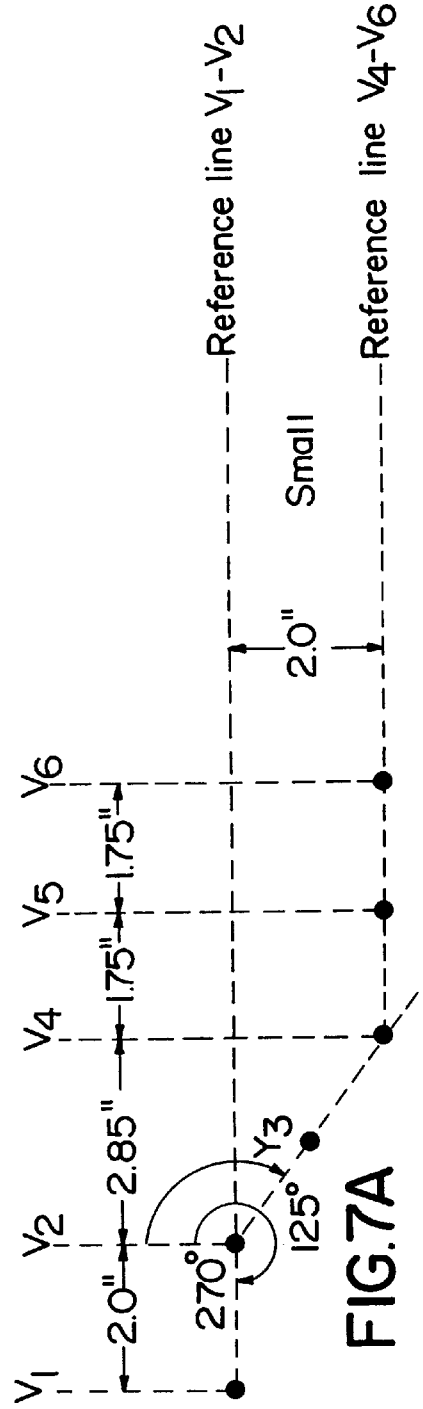
FIGS. 7A–7C show a dimensional layout of a small, medium and large template according to this invention.
Figure 7B:
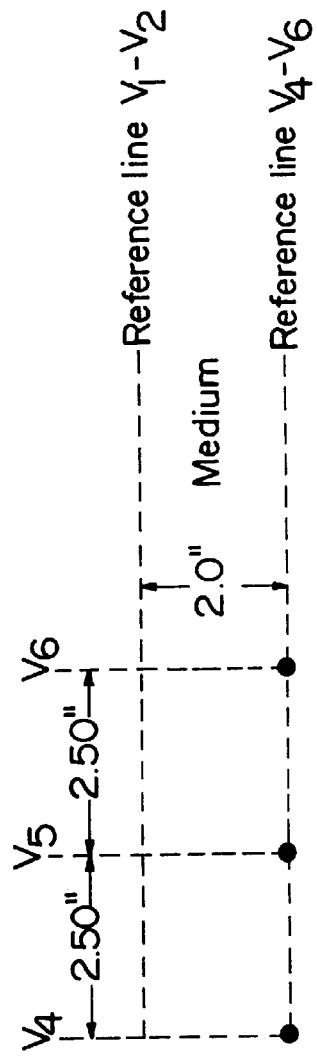
Figure 7C:
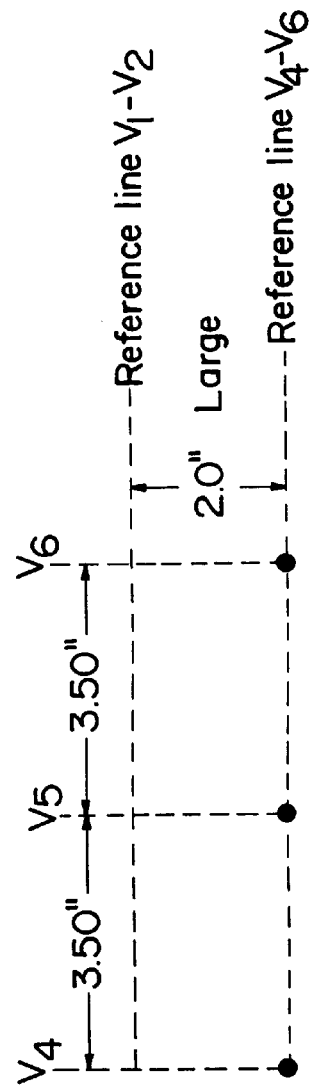

A typical dimensional layout for $V_5$ and $V_6$ relative to $V_4$ is shown in FIGS. 7A, 7B and 7C, and is as follows:

TABLE II

| SIZE | $V_4$–$V_5$ | $V_5$–$V_6$ |
|---|---|---|
| Small | 1.75" | 1.75" |
| Medium | 2.50" | 2.50" |
| Large | 3.50" | 3.50" |

The distance between $V_1$ and $V_2$ is 2.00 inches, the distance between sternum centerline and $V_4$ along a horizontal line is 3.85 inches and the distance between $V_2$ and $V_4$ along a vertical line is 2.00 inches, although this vertical distance could be up to 3.50 inches without considerably altering the effectiveness of the device. In addition, $V_3$ is located on a diagonal line between $V_2$ and $V_4$ and is equidistant from $V_2$ and $V_4$.

As discussed above, the connector device can be sized to accommodate practically any size adult person. Even if the person is smaller than the "small" size device, a connector device of the small (or even medium or large) size can be used by folding the flexible sheet 11 over on itself to reduce the distances between the connector arrays as appropriate.

As will be appreciated, the embodiment shown in FIGS. 1–7C provides a plurality of connectors arranged in a predetermined dimensional array $V_1$–$V_6$ on the flexible sheet. In providing alternative embodiments of the present invention, the dimensional array on the flexible sheet is utilized, and the specific size configuration of the dimensional array, or layout, on the flexible sheet is determined in the same manner as described above. In the following embodiments, however, the connectors (and attendant ends sensors 22, conductor strips 12 and terminal connectors ends 23) are removed, and the predetermined dimensional array is used in alternative ways to provide a consistent electrocardial recording.

Figure 8:
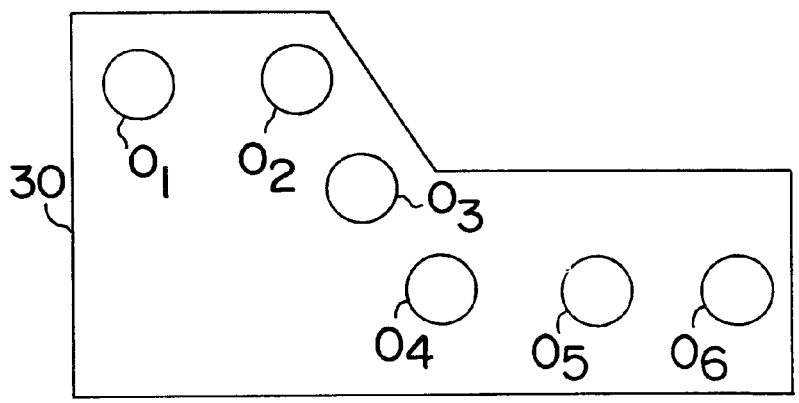
FIG. 8 shows another embodiment of the present invention for attachment to the torso of the patient.

In the embodiment shown in FIG. 8, a flexible sheet 30, which is comparable to the flexible sheet 11, is provided with a plurality of spaced openings $O_1$–$O_6$, or cutouts, for positioning electrodes on the patient's chest. The openings $O_1$–$O_6$ are positioned in the predetermined dimensional array $V_1$–$V_6$ in the same manner as described above to accommodate almost any size adult person.

In use, the flexible sheet is placed on the patient's chest, and serves as a template to position an electrode within each opening.

Figure 9A:
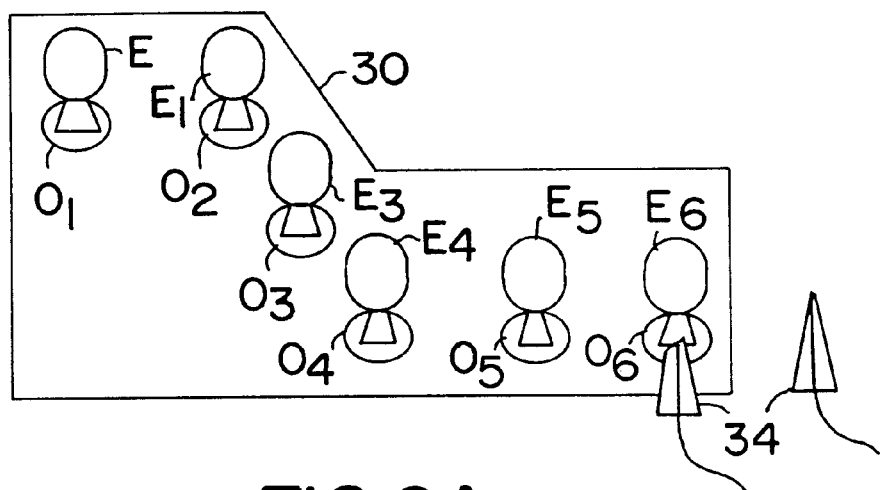
FIGS. 9A and 9B show still another embodiment of the present invention for attachment to the torso of the patient.
Figure 9B:
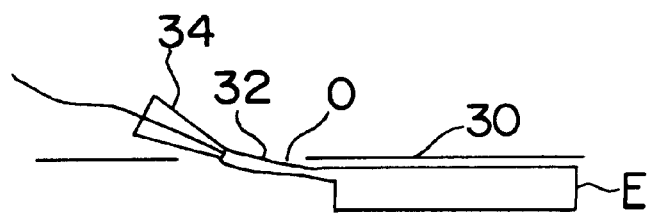

FIGS. 9A and 9B show another embodiment in which flexible sheet 30 is provided with a plurality of conventional tab electrodes $E_1$–$E_6$ and small openings $O_1$–$O_6$ proximate to the electrodes.

The electrodes $E_1$–$E_6$ are positioned in a predetermined dimensional array $V_1$–$V_6$ in the same manner as the sensors to accommodate almost any size adult person. As best seen in FIG. 9B, top sides of the tab electrodes are affixed to the flexible sheet and the small openings $O_1$–$O_6$ expose electrical tabs 32 for attaching lead wire clips 34.

Figure 10A:
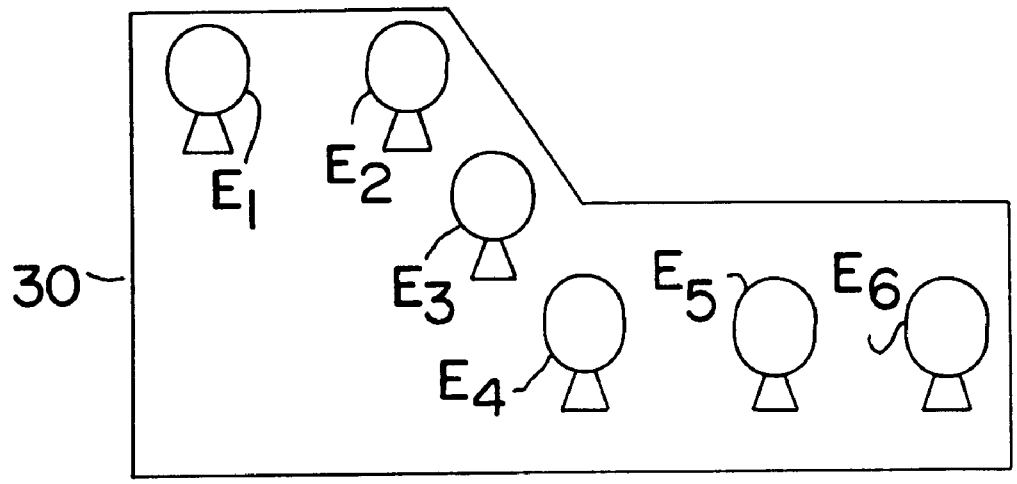
FIGS. 10A and 10B show yet another embodiment of the present invention for attaching electrodes to the torso of the patient.

In another embodiment, individual electrodes $E_1$–$E_6$ are detachably affixed to the flexible sheet 30 as shown in FIG. 10A. In this arrangement, top sides of the electrodes are lightly affixed to the flexible sheet in the same predetermined dimensional array disclosed above.

Figure 10B:
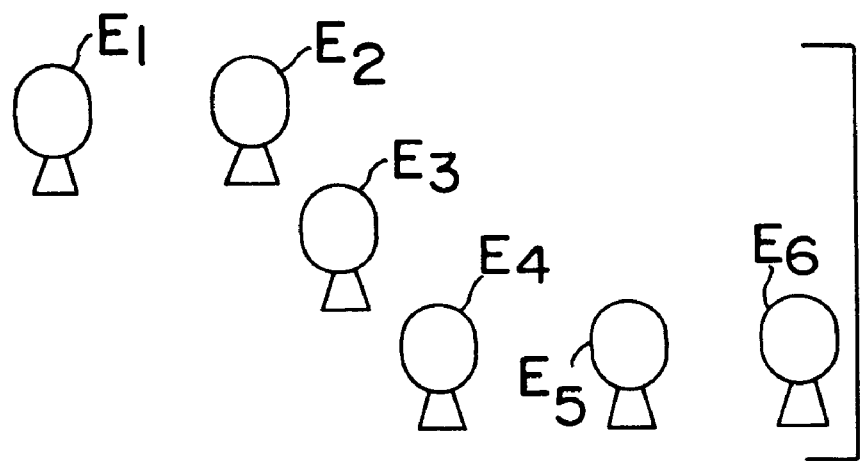

In use, the flexible sheet and electrodes are placed on the patient's chest. The flexible sheet is then peeled away, leaving the individual electrodes properly located on the chest (see FIG. 10B).

Although not shown, it will be appreciated that the flexible sheet 30 shown in FIGS. 8, 9A, 9B and 10A can be provided with an opening in the proximate center as shown in FIG. 1 to assist in positioning the sheet on the patient's chest.

Although specific embodiments of the present invention have been described above in detail, it will be understood that this description is merely for purposes of illustration. Various modifications of and equivalent structures corresponding to the disclosed aspects of the preferred embodiments in addition to those described above may be made by those skilled in the art without departing from the spirit of the present invention which is defined in the following claims, the scope of which is to be accorded the broadest interpretation so as to encompass such modifications and equivalent structures.

What is claimed is:

1. An electro-dermal sensor positioning device comprising a substrate having a fixed array $V_1$–$V_6$ of receptor positions positioned in a specific size configuration appropriate for electrocardiographic recording, with said receptor positions $V_1$, $V_2$, $V_3$ and $V_4$ positioned at predetermined fixed locations on said sheet and said receptor positions $V_5$ and $V_6$ positioned at predetermined fixed locations on said substrate which vary dependent on patient size, wherein:

the distance between $V_1$ and $V_2$ is approximately 1.50 to 2.50 inches and the distance between $V_2$ and $V_4$ is approximately 2.50 to 4.50 inches, with $V_3$ located substantially midway between $V_2$ and $V_4$, and $V_5$ being substantially equidistant between $V_4$ and $V_6$.

2. The device of claim 1, wherein the distance between $V_4$ and $V_5$ and between $V_5$ and $V_6$ is about 1.75 inches.

3. The device of claim 1, wherein the distance between $V_4$ and $V_5$ and between $V_5$ and $V_6$ is about 2.5 inches.

4. The device of claim 1, wherein the distance between $V_4$ and $V_5$ and between $V_5$ and $V_6$ is about 3.5 inches.

5. The device of claim 1, wherein $V_1$ is located approximately 1.50 to 2.50 inches in radius on about a 270 degree radial from the center of $V_2$.

6. The device of claim 1, wherein $V_3$ is located on about a 125 degree radial from the center of $V_2$.

7. The device of claim 1, wherein $V_4$ is located on about a 125 degree radial from the center of $V_2$.

8. A device according to claim 1, wherein the distance between $V_2$ and $V_4$ ranges between 2 and 4.5 inches.

9. A device according to claim 1, wherein a vertical distance between $V_2$ and $V_4$ is approximately 2.5 to 3.5 inches.

10. A positioning device of claim 1, wherein said substrate is disposable.

11. The device of claim 1, wherein $V_5$ and $V_6$ can be positioned at three different locations on the substrate.

12. The device of claim 1, wherein said substrate is selected from nonconductive flexible natural or synthetic material.

13. The device of claim 12, wherein said substrate is selected from cellulosic materials, polyesters, polyolefins, polyvinyl chloride or nylon.

14. The device of claim 13, wherein said cellulosic material is cotton or paper.

15. The device of claim 13, wherein said polyester is polyethylene terphthalate.

16. A process of forming an electro-dermal sensor positioning device for electrocardiographic recording, comprising the steps of:

providing a substrate with a fixed array $V_1$–$V_6$ of receptor positions positioned in a specific size configuration appropriate for electrocardiographic recording;

positioning receptor positions $V_1$, $V_2$, $V_3$ and $V_4$ at predetermined locations on the substrate;

positioning receptor positions $V_5$ and $V_6$ at fixed locations on the substrate which vary dependent on patient size; and positioning the receptor positions $V_1$–$V_6$ such that the distance between $V_1$ and $V_2$ is approximately 1.50 to 2.50 inches, and the distance between $V_2$ and $V_4$ is approximately 2.50 to 4.50 inches, with $V_3$ located substantially midway between $V_2$ and $V_4$, and $V_5$ substantially equidistant between $V_4$ and $V_6$.

17. A process according to claim 16, further comprising the step of positioning receptor positions $V_5$ and $V_6$ based on a distance between a midclavicular line and a midaxillary line on the chest of the patient.

18. A process according to claim 16, further comprising the step of positioning receptor positions $V_1$ and $V_2$ to be approximately on either side of the sternum at the fourth intercostal space and positioning array $V_3$ to be approximately midway between $V_2$ and $V_4$.

19. A process according to claim 16, wherein the distance between $V_4$ and $V_5$ and between $V_5$ and $V_6$ for a small size is about 1.75 inches, for a medium size is about 2.5 inches, and for a large size is about 3.5 inches.

20. A process according to claim 16, wherein $V_1$ is located approximately between 1.50–2.50 inches in radius on about a 270 degree radial from the center of $V_2$.

21. A process according to claim 16, wherein $V_3$ is located on about a 125 degree radial from the center of $V_2$.

22. A process according to claim 16, wherein $V_4$ is located on about a 125 degree radial from the center of $V_2$.

23. A process according to claim 16, further comprising the step of providing a disposable substrate.

24. The process of claim 16, wherein $V_5$ and $V_6$ can be positioned at three different locations on the substrate.

25. A plurality of sensor positioning devices of different sizes, with each device comprising:

a substrate with a fixed array $V_1$–$V_6$ of receptor positions positioned in a specific size configuration appropriate for electrocardiographic recording, with the receptor positions $V_1$, $V_2$, $V_3$ and $V_4$ positioned at substantially the same locations on each said size, and receptor positions $V_5$ and $V_6$ positioned differently on each said size dependent upon the size of the patient.

26. The devices of claim 25, wherein in each said device the distance between $V_1$ and $V_2$ is approximately 1.50 and 2.50 inches and the distance between $V_2$ and $V_4$ is approximately 2.50 and 4.50 inches, with $V_3$ located substantially midway between $V_2$ and $V_4$, and $V_5$ is substantially equidistant between $V_4$ and $V_6$.

27. A device according to claim 26, wherein a vertical distance between $V_2$ and $V_4$ is approximately 2.0 to 3.5 inches.

28. The devices of claim 25, wherein three sizes of said devices are provided, with the distance between $V_4$ and $V_5$ and between $V_5$ and $V_6$ for a small size being about 1.75 inches, for a medium size being about 2.5 inches, and for a large size being about 3.5 inches.

29. The devices of claim 25, wherein in each said device $V_1$ is located approximately between 1.50 and 2.50 inches in radius on about a 270 degree radial from the center of $V_2$.

30. The devices of claim 25, wherein in each said device $V_3$ is located on about a 125 degree radial from the center of $V_2$.

31. The devices of claim 25, wherein in each said device $V_4$ is located on about a 125 degree radial from the center of $V_2$.

32. The device of claim 25, wherein said substrate is disposable.

33. An electro-dermal sensor positioning device comprising a flexible substrate having a fixed array $V_1$–$V_6$ of receptor positions positioned in a specific size configuration appropriate for electrocardiographic recording, with said receptor positions $V_1$, $V_2$, $V_3$ and $V_4$ positioned at predetermined fixed locations on said substrate and said receptor positions $V_5$ and $V_6$ positioned at predetermined fixed locations on said substrate which vary dependent on patient size, wherein:

$V_1$ is located approximately between 1.50 and 2.50 inches in radius on about a 270 degree radial from the center of $V_2$.

34. The device of claim 33, wherein said substrate is disposable.

35. The device of claim 33, wherein said substrate is selected from nonconductive flexible natural or synthetic material.

36. The device of claim 35, wherein said substrate is selected from cellulosic materials, polyesters, polyolefins, polyvinyl chloride or nylon.

37. The device of claim 36, wherein said cellulosic material is cotton or paper.

38. The device of claim 36, wherein said polyester is polyethylene terphthalate.

39. A process of forming an electro-dermal sensor positioning device for electrocardiographic recording, comprising the steps of:

providing a substrate with a fixed array $V_1$–$V_6$ of receptor positions positioned in a specific size configuration appropriate for electrocardiographic recording;

positioning receptor positions $V_1$, $V_2$, $V_3$ and $V_4$ at predetermined locations on the substrate; and positioning receptor positions $V_5$ and $V_6$ at fixed locations on the sheet which vary dependent on patient size, wherein $V_1$ is located approximately between 1.50 and 2.50 inches in radius on about a 270 degree radial from the center of $V_2$.

40. A process of claim 39, further comprising the step of providing a disposable substrate.

41. A process of forming a plurality of sensor positioning devices of different sizes, comprising the steps of:

providing a plurality of flexible substrates, each with a fixed array $V_1$–$V_6$ of receptor positions positioned in a specific size configuration appropriate for electrocardiographic recording;

positioning receptor positions $V_1$, $V_2$, $V_3$ and $V_4$ at substantially the same locations on each size substrate; and positioning receptor positions $V_5$ and $V_6$ differently on each size substrate dependent upon the size of the patient.

42. A process according to claim 41, further comprising the step of positioning receptor positions $V_1$–$V_6$ on each size substrate, such that the distance between $V_1$ and $V_2$ is 2.00 inches±0.56 inches and the distance between $V_2$ and $V_4$ is 3.5 inches±1.00 inch, with $V_3$ located substantially midway between $V_2$ and $V_4$, and $V_5$ is substantially equidistant between $V_4$ and $V_6$.

43. A process according to claim 41, wherein the receptor positions $V_5$ and $V_6$ are positioned at fixed locations based on a measured distance between a midclavicular line and a midaxillary line on the chest of the patient, with the fixed locations varying for each size substrate.

44. A process according to claim 41, further comprising the step of, on each size substrate, positioning receptor positions $V_1$ and $V_2$ to be approximately on either side of the sternum at the fourth intercostal space and positioning $V_3$ to be approximately midway between $V_2$ and $V_4$.

45. A process according to claim 41, wherein three electro-dermal sensor positioning devices are formed, with the distance between $V_4$ and $V_6$ and between $V_5$ and $V_6$ for a small size device being about 1.75 inches, for a medium size device being about 2.5 inches, and for a large size device being about 3.5 inches.

46. A process according to claim 41, wherein $V_1$ on each size substrate is located 2.00 inches±0.56 inches in radius on about a 270 degree radial from the center of $V_2$.

47. A process according to claim 41, wherein $V_3$ and $V_4$ on each size substrate are located on about a 125 degree radial from the center of $V_2$.

48. A process of claim 41, further comprising the steps of providing a plurality of disposable substrates.

* * * * *